(12) United States Patent
Bender et al.

(10) Patent No.: US 7,645,736 B2
(45) Date of Patent: Jan. 12, 2010

(54) INTEGRIN INHIBITORS FOR THE TREATMENT OF EYE DISEASES

(75) Inventors: Hans-Markus Bender, Ostermünchen (DE); Jutta Haunschild, München (DE); Ulrich Lang, Heppenheim (DE); Matthias Wiesner, Mainz (DE); Martin Friedlander, Del Mar, CA (US)

(73) Assignee: Merck Patent GmbH, Darmstadt (DE)

( * ) Notice: Subject to any disclaimer, the term of this patent is extended or adjusted under 35 U.S.C. 154(b) by 344 days.

(21) Appl. No.: 11/510,596

(22) Filed: Aug. 28, 2006

(65) Prior Publication Data

US 2006/0287225 A1    Dec. 21, 2006

Related U.S. Application Data

(62) Division of application No. 10/485,386, filed on Jan. 30, 2004, now abandoned.

(51) Int. Cl.
*A61K 38/00* (2006.01)
(52) U.S. Cl. .......................................................... 514/2
(58) Field of Classification Search ........................ None
See application file for complete search history.

(56) References Cited

U.S. PATENT DOCUMENTS

| | | | |
|---|---|---|---|
| 6,378,526 B1 * | 4/2002 | Bowman et al. | 128/898 |
| 6,489,305 B1 * | 12/2002 | Demers | 514/44 |
| 6,500,924 B1 * | 12/2002 | Brooks et al. | 530/350 |

FOREIGN PATENT DOCUMENTS

| | | |
|---|---|---|
| WO | 97 06791 | 2/1997 |
| WO | 97 14716 | 4/1997 |
| WO | 97 34586 | 9/1997 |
| WO | WO 9745137 A1 * | 12/1997 |
| WO | 98 35949 | 8/1998 |
| WO | 99 45909 | 9/1999 |
| WO | 00 26212 | 5/2000 |
| WO | 01 58893 | 8/2001 |

OTHER PUBLICATIONS

M. Friedlander, et al. Proc. Natl. Acad. Sci. USA (1996) 93, pp. 9764-9769.*
M. Kamei, et al. Am. J. Ophthalmol. (1999) 128, pp. 739-746.*
("MACUGEN® Therapy" Southwestern Medical Center, http://www8.utsouthwestern.edu/utsw/cda/dept28070/files/201632.html, accessed Apr. 25, 2005, 3 pages.*
S. Henahan, "New strategies to prevent blindness" Access Excellence. Oct. 21, 1999, 4 pages.*
G.A. Peyman and J.A. Schulman. Jpn. J. Ophthalmol. (1989) 33(4), pp. 392-404.*
k.J. Tojo and A. Ohtori. Math. Biosci. (1994) 123(1), pp. 59-75.*
Intravitreal Triamcinolone (ivTA) for diabetitc macular edema. Fact Sheet, 2 pages. (2005).*
Intravitreal Triamcinolone, North Shore Eye Center, 3 pages. (2005).*
DB Mak, et al. Clin. Exp. Ophthal. (2001) 29, pp. 7-11.*
A Shafiee, et al. Invest. Ophthal. Visual Sci. (2000) 41, pp. 2378-2388.*
"Histoplasmosis" The Clevland Clinic. [internet document] <http://www.clevlandclinic.org/ health/health-info/docs/0900/0998. asp?index=5635&src=news>; Accessed Oct. 17, 2005, 4 pages.*
"Nearsightedness" MedlinePlus Medical Encyclopedia, 2 pages. updated Jan. 19, 2004, retrieved Oct. 17, 2005.*

* cited by examiner

*Primary Examiner*—Andrew D Kosar
(74) *Attorney, Agent, or Firm*—Millen, White, Zelano, Branigan, P.C.

(57) ABSTRACT

Methods for the treatment of a disease of the eye of a patient comprising injecting into the vitreous body of the eye a composition comprising a therapeutically effective amount of an $\alpha_v\beta_3$ and/or $\alpha_v\beta_5$ inhibitor sufficient to inhibit angiogenesis and inhibit neovascularization in the treated eye. The $\alpha_v\beta_3$ and/or $\alpha_v\beta_5$ inhibitor being a compound of formula II:

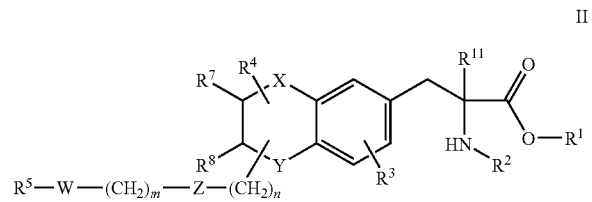

as defined herein or a physiologically acceptable salt thereof.

23 Claims, No Drawings

INTEGRIN INHIBITORS FOR THE TREATMENT OF EYE DISEASES

This application is a divisional of U.S. Ser. No. 10/485,386, filed Jan. 30, 2004, now abandoned.

TECHNICAL FIELD

The present invention relates generally to the field of medicine, and relates specifically to methods and compositions for the prophylaxis and/or treatment of diseases of the eye using antagonists of the integin receptors $\alpha_v\beta_3$ and/or $\alpha_v\beta_5$. More specifically, the invention relates to methods and compositions for the prophylaxis and/or treatment of diseases of the eye using antagonists of the integrin receptors $\alpha_v\beta_3$ and/or $\alpha_v\beta_5$ wherein the compositions are administered by injection into the vitreous body of the eye.

BACKGROUND

Integrins are a class of cellular receptors known to bind extracellular matrix proteins, and therefore mediate cell-cell and cell-extracellular matrix interactions, referred generally to as adhäsion events. Integrins receptors constitute a family of proteins across membranes with shared structural characteristics heterodimeric glycoprotein complexes formed of $\alpha$ and $\beta$ subunits.

One class of integrin receptors, the vitronectin receptor, named for its original characteristic of preferential binding to vitronectin, is known to refer to three different integrins, designated. $\alpha_v\beta_1$, $\alpha_v\beta_3$ and $\alpha_v\beta_5$. Horton, Int. J. Exp. Pathol., 71:741-759 (1990). $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteospontin and bone sialoprotein I. $\alpha_v\beta_5$ binds vitronectin. The specific cell adhesion roles these three integrins play in the many cellular interactions in tissues is still under investigation, but it is clear that there are different integrins with different biological functions.

One important recognition site in the ligand for many integrins is the arginine-glycine-aspartic acid (RGD) tripeptide sequence. RGD is found in all of the ligands identified above for the vitronectin receptor integrins. This RGD recognition site can be mimicked by polypeptides ("peptides") that contain the RGD sequence, and such RGD peptides are known inhibitors of integrin function.

Integrin inhibitors containing the RGD sequence are disclosed, for example, in EP 0 770 622 A2. The compounds described inhibit in particular the interactions of $\beta_3$- and/or $\beta_5$-integrin receptors with ligands and are particularly active in the case of the integrins $\alpha_v\beta_3$, $\alpha_v\beta_5$ and $a_{IIb}\beta_3$, but also relative to $\alpha_v\beta_1$, $\alpha_v\beta_6$ and $\alpha_v\beta_8$ receptors. These actions can be demonstrated, for example, according to the method described by J. W. Smith et al. in J. Biol. Chem. 265, 12267-12271 (1990). In addition, the compounds possess anti-inflammatory effects.

On basis of integrin inhibitors containing the RGD sequence a multitude of antagonists without the RGD sequence have been made available. Those integrin inhibitors without RGD sequence are disclosed, for example, in WO 96/00730 A1, WO 96/18602 A1, WO 97/37655 A1, WO 97/06791 A1, WO 97/45137 A1, WO 97/23451 A1, WO 97/23480 A1, WO 97/44333 A1, WO 98/00395 A1, WO 98/14192 A1, WO 98/30542 A1, WO 99/11626 A1, WO 99/15178 A1, WO 99/15508 A1, WO 99/26945 A1, WO 99/44994 A1, WO 99/45927 A1, WO 99/50249 A2, WO 00/03973 A1, WO 00/09143 A1, WO 00/09503 A1, WO 00/33838 A1.

DE 1970540 A1 disclose bicyclic aromatic amino acids acting as integrin inhibitors of the $\alpha_v$ integrin receptors, particulary of the integrins $\alpha_v\beta_3$ and $\alpha_v\beta_5$. The compounds are very particularly active as adhesion receptor antagonists for the vitronectin receptor $\alpha_v\beta_3$. This effect can be demonstrated, for example, by the method described by J. W. Smith et al. in J. Biol. Chem. 265, 11008-11013 and 12267-12271 (1990).

WO 00/26212 A1 discloses chromenone and chromanone derivatives acting as integrin inhibitors of the $\alpha_v$ integrin receptors, particulary of the integrins $\alpha_v\beta_3$ and $\alpha_v\beta_5$. The compounds are also very particularly active as adhesion receptor antagonists for the vitronectin receptor $\alpha_v\beta_3$.

Integrin inhibitors have been suggested as pharmaceutically active principle in human and veterinary medicine, in particular for the prophylaxis and treatment of various disorders. Specifically suggested have been their use for the treatment and prophylaxis of the circulation, thrombosis, cardiac infarction, arteriosclerosis, inflammations, apoplexy, angina pectoris, tumor disorders, osteolytic disorders, especially osteoporosis, angiogenesis and disorders resulting from angiogenesis, for example diabetic retinopathy of the eye, macular degeneration, myopia, ocular histoplasmosis, rheumatic arthritis, osteoarthritis, rubeotic glaucoma, and also ulcerative colitis, Crohn's disease, multiple sclerosis, psoriasis and restenosis following angioplasty.

Eye diseases resulting from angiogenesis are the leading cause of visual loss in America. While in case of the population of the age of over 65 visual loss is predominantly effected by age-related macular degeneration (AMD) in case of population of the age of less than 65 this is predominantly effected by diabetic retinopathy.

In Wall Street Journal from Mar. 6 th, 2000 an overview about occurence and current therapies of AMD is given. According to this AMD currently afflicts some 12 million Americans. AMD progressively destroys the macula which is responsible for central vision and color vision. In some cases, deterioration of central vision to fuzzy blur can be rapid occuring in weeks or months. Two forms of the disease exists called "atrophic" and "exudative". Although exudative AMD effects only 10% of the total AMD population, it accounts for 90% of all AMD-related blindness.

Until recently, the only treatment for exudative AMD consisted of directing a powerful laser beam at the harmful blood vessels to heat and coagulate them. However, only about 15% of patients with exudative AMD have been eligible for this laser surgery. Other therapies are currently in experimental phase. In one approach, called photodynamic therapy, a low-power laser is combined with injection of light-absorbing dye. Another therapy is a more surgical approach and is called "limited retinal translocation". In this therapy the leaky vessels are destroyed with a high-powered laser after separation and rotation of the retina from the outer-wall of the eye.

U.S. Pat. No. 5,766,591 describes the use of RGD-containing $\alpha_v\beta_3$ antagonists for the treatment of patients in which neovascularisation in the retinal tissue occurs. More specifically the use of said antagonists for the treatment of patients with diabetic retinopathy, macular degeneration and neovasular glaucoma is suggested. However, no examples with regard to this indications are presented. Concerning to the route of administration only general information are given. Specifically intravenous, intraperitoneal, intramuscular, intracavital and transdermal application is mentioned. In all cases $\alpha_v\beta_3$ antagonists are preferred exhibiting selectivity for $\alpha_v\beta_3$ over other integrins such as $\alpha_v\beta_5$.

WO 97/06791 A1 describes that $\alpha_v\beta_5$ antagonists can be used for inhibiting angiogenesis too. Likewise as suggested for $\alpha_v\beta_3$ antagonists in U.S. Pat. No. 5,766,591 $\alpha_v\beta_5$ antagonists are suggested for the treatment of a patient with diabetic retinopathy, macular degeneration and neovasular glaucoma. With regard to the route of administration intravenous, intraocular, intrasynovial, intramuscular, transdermal and oral application is specifically mentioned.

DESCIPTION OF THE INVENTION

It has been found that inhibitors of $\alpha_v\beta_3$ and/or $\alpha_v\beta_5$ integrin receptors have particularly useful pharmacological and physicochemical properties combined with good tolerability, as, in particular, they can be used for prophylaxis and treatment of diseases of the eye of a patient resulting from angiogenesis in the eye by injecting the inhibitor into the vitreous body of the eye.

Accordingly, the invention is directed to a method for prophylaxis and/or treatment of diseases of the eye of a patient resulting from angiogenesis in the eye comprising injecting into the vitreous body of the eye of said patient a composition comprising a therapeutically effective amount of an $\alpha_v\beta_3$ and/or $\alpha_v\beta_5$ inhibitor sufficient to inhibit angiogenesis of the eye.

The vitreous body is disposed within a posterior portion of the eye and occupies approximately four fifths of the cavity of the eyeball, behind the lens. The vitreous body is formed of gelatinous material, known as the vitreous humor. The vitreous humor of a normal human eye is made up of approximately 99% water along with 1% macromolecules including collagen, hyaluronic acid, soluble glycoproteins, sugars and other low molecular weight metabolites.

For application of the drug into the vitreous the $\alpha_v\beta_3$ and/or $\alpha_v\beta_5$ inhibitor sufficient to inhibit angiogenesis of the eye can can be directly injected into the vitreous body, via a needle passed through the pars plana.

A therapeutically effective amount is an amount of inhibitor sufficient to produce a measureable inhibition of angiogenesis in the tissue of the eye when injected into the vitreous body. In general, this is the case when the $\alpha_v\beta_3$ and/or $\alpha_v\beta_5$ inhibitor is used in an amount from about 0.5 µg to about 5 mg.

The method of invention is especially usable for prophylaxis and/or treatment of diabetic retinopathy, macular degeneration, myopia and histoplasmosis.

In a preferred embodiment of the invention polypeptides containing the amino acid sequence RGD are used as $\alpha_v\beta_3$ and/or $\alpha_v\beta_5$ inhibitors in the method for prophylaxis and/or treatment of eye diseases. As mentioned above, RGD is the peptide sequence Arg-Gly-Asp (arginine-glycine-aspartic acid) occuring in natural ligands of integrins like fibronectin or vitronectin. Solvable RGD containing linear or cyclic peptides are able to inhibit interactions of this integrins with their corresponding natural ligands.

The abbreviations for the amino acid residues used hereinafter are shown in the following table:

| Ala | A | alanine |
|---|---|---|
| Arg | R | arginine |
| Asp | D | aspartic acid |
| D-homoPhe | | D-homo-phenylalanine |
| D-Nal | | D-3-(2-naphthyl)alanine |
| D-Phe | | D-phenylalanine |
| D-Phg | | D-phenylglycine |
| D-Trp | | D-tryptophan |
| D-Tyr | | D-tyrosine |
| Gly | G | glycine |

-continued

| 4-Hal-Phe | | 4-halo-phenylalanine |
|---|---|---|
| homoPhe | | homo-phenylalanine |
| Ile | I | isoleucine |
| Leu | L | leucine |
| Nal | | 3-(2-naphthyl)alanine |
| Nle | | norleucine |
| Phe | F | phenylalanine |
| Phg | | phenylglycine |
| Trp | W | tryptophan |
| Tyr | Y | tyrosine |
| Val | V | valine. |

Particularly preferred as $\alpha_v\beta_3$ and/or $\alpha_v\beta_5$ inhibitors to be used in the method for prophylaxis and/or treatment of eye diseases are compounds of formula I $$\text{cyclo-(Arg-Gly-Asp-D-(A)}_n\text{E)} \qquad \text{I,}$$

in which

D is D-Phe, Phe, D-Trp, Trp, D-Tyr, Tyr, D-homoPhe, homoPhe, D-Nal, Nal, D-Phg, Phg or 4-Hal-Phe (D or L form), in which Hal is F, Cl, Br, I, E is Val, Gly, Ala, Leu, Ile or Nle, A is alkyl having 1-18 carbon atoms and n is 0 or 1 and also their physiologically acceptable salts.

In formula I alkyl is preferably methyl, ethyl, isopropyl, n-butyl, sec-butyl or tert-butyl.

More particular preferred polypeptides are used as $\alpha_v\beta_3$ and/or $\alpha_v\beta_5$ inhibitors in the method of the invention that can be expressed by the subformula Ia, which otherwise corresponds to the formula I but in which D is D-Phe and E is Gly, Ala, Val, Leu, Ile or Nle.

Furthermore, particular preference is given to the use of all physiologically compatible salts of the compounds which come under the subformula Ia.

Most preferred as active compound in said method are cyclo-(Arg-Gly-Asp-DPhe-Val) and cyclo-(Arg-Gly-Asp-DPhe-NMeVal).

This RGD-containing peptides described by formula I as well as the peptides specifically mentioned hereinbefore are disclosed in EP 0 770 622 A2, the disclosure of which is hereby incorporated to the present application by reference. Accordingly, the meaning of the substituents of formula I resp. subformula Ia are the same as defined for the substituents of subformula Ia resp. subformula Ib as disclosed on page 5, line 24 to line 32 resp. page 5, line 33 to line 41 in EP 0 770 662 A2.

It has been found that inhibitors of $\alpha_v\beta_3$ and/or $\alpha_v\beta_5$ integrin receptors which are no polypeptides and do not contain the RGD sequence can also be used for prophylaxis and treatment of diseases of the eye of a patient resulting from angiogenesis in the eye by injecting the inhibitor into the vitreous body of the eye.

Therefore, in one further preferred embodiment of the method of invention the $\alpha_v\beta_3$ and/or $\alpha_v\beta_5$ inhibitors to be used in the method for prophylaxis or treatment of eye diseases are compounds of formula II

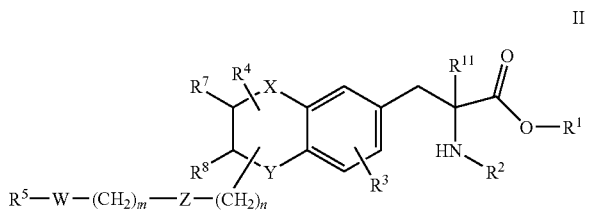

wherein
$R^1$ is H, alkyl having 1-6 C atoms or benzyl,
$R^2$ is $R^{10}$, CO—$R^{10}$, COOR$^6$, COOR$^{10}$, SO$_2$R$^6$ or SO$_2$R$^{10}$,
$R^3$ is H, Hal, OA, NHR$^{10}$, N(R$^{10}$)$_2$, —NH-acyl, —O-acyl, CN, NO$_2$, OR$^{10}$, SR$^{10}$, R$^2$ or CONHR$^{10}$,
$R^4$ is H, =O, =S, C$_1$-C$_6$-alkyl or acyl,
$R^5$ is NH$_2$, H$_2$N—C(=NH) or H$_2$N—(C=NH)—NH, where the primary amino groups can also be provided with conventional amino protective groups or can be mono-, di- or trisubstituted by R$^{10}$, CO—R$^{10}$, COOR$^{10}$ or SO$_2$R$^{10}$, or R$^6$,
$R^7$, $R^8$ are each independently of one another absent or H,
$R^7$ and $R^8$ together are also a bond,
X, Y are each independently of one another =N—, —N—, O, S, —CH$_2$— or =C—, with the proviso that at least one of the two definitions X, Y is =N—, —N—, O or S,
W, Z are each independently of one another absent, O, S, NR$^1$, C(=O), CONH, NHCO, C(=S)NH, NHC(=S), C(=S), SO$_2$NH, NHSO$_2$ or CA=CA',
$R^6$ is a mono- or binuclear heterocycle which has 1 to 4 N, O and/or S atoms and can be unsubstituted or mono-, di- or trisubstituted by Hal, A, —CO—A, OH, CN, COOH, COOA, CONH$_2$, NO$_2$, =NH or =O,
$R^9$ is H, Hal, OA, NHA, NAA', NHacyl, Oacyl, CN, NO$_2$, SA, SOA, SO$_2$A, SO$_2$Ar or SO$_3$H,
$R^{10}$ is H, A, Ar or aralkyl having 7-14 C atoms,
$R^{11}$ is H or alkyl having 1-6 C atoms,
A, A' are each independently of one another H or unsubstituted or mono-, di- or tri-R$^9$-substituted alkyl or cycloalkyl, each of which has 1-15 C atoms and in which one, two or three methylene groups can be replaced by N, O and/or S,
Ar is unsubstituted or mono-, di- or tri-A- and/or R$^9$-substituted mono- or binuclear aromatic ring system having 0, 1, 2, 3 or 4 N, O and/or S atoms,
Hal is F, Cl, Br or I and
m, n are each independently of one another 0, 1, 2, 3 or 4, and the physiologically acceptable salts thereof.

Particularly preferred $\alpha_v\beta_3$ and/or $\alpha_v\beta_5$ inhibitors are used in the method of invention that can be expressed by the subformulae IIa to IIg, which otherwise corresponds to the formula II but in which in IIa)
$R^1$ is H or alkyl with 1-6 C atoms,
$R^2$ is R$^{10}$, CO—R$^{10}$, COOR$^{10}$ or SO$_2$R$^{10}$,
$R^3$ is H,
$R^4$ is H or =O,
$R^5$ is H$_2$N—C(=NH) or H$_2$N—C(=N)—NH,
W, Z are each independently of one another absent, C(=O), NH, CONH or NHCO,
X is —NH—, O or —CH$_2$—,
Y is NH or O,
$R^{10}$ is H, A or benzyl,
$R^{11}$ is H,
A is unsubstituted alkyl or cycloalkyl with 1-15 C atoms and
m, n are each independently of one another 0, 1 or 2;
in IIb)
$R^1$ is H or alkyl with 1-6 C atoms,
$R^2$ is R$^{10}$, CO—R$^{10}$, COOR$^{10}$ or SO$_2$R$^{10}$,
$R^3$ is H,
$R^4$ is H or =O,
$R^5$ is R$^6$,
W, Z are each independently of one another absent, C(=O), NH, CONH or NHCO,
X is —NH—, O or —CH$_2$—,
Y is NH or O,
$R^6$ is a mono- or binuclear heterocycle which has 1-4 N, O and/or S atoms and which can be unsubstituted or mono-, di- or trisubstituted by Hal, A, —CO—A, OH, CN, COOH, COOA, CONH$_2$, NO$_2$, =NH or =O,
$R^{10}$ is H, A or benzyl,
$R^{11}$ is H,
A is unsubstituted alkyl or cycloalkyl with 1-15 C atoms and
m, n are each independently of one another 0, 1 or 2;
in IIc)
$R^1$ is H or alkyl with 1-6 C atoms,
$R^2$ is R$^{10}$, CO—R$^{10}$, COOR$^{10}$ or SO$_2$R$^{10}$,
$R^3$ is H,
$R^4$ is H or =O,
$R^5$ is H$_2$N—C(=NH) or H$_2$N—C(=NH)—NH,
W, Z are each independently of one another absent, C(=O), NH, CONH or NHCO,
X is —NH—, O or —CH$_2$—,
Y is NH or O,
A is alkyl with 1-6 C atoms,
$R^{10}$ is H, alkyl with 1-6 C atoms, camphor-10-yl or benzyl,
$R^{11}$ is H,
m, n are each independently of one another 0, 1 or 2;
in IId)
$R^1$ is H or alkyl with 1-6 C atoms,
$R^2$ is R$^{10}$, CO—R$^{10}$, COOR$^{10}$ or SO$_2$R$^{10}$,
$R^3$ is H,
$R^4$ is H or =O,
$R^5$ is R$^6$,
W, Z are each independently of one another absent, C(=O), NH, CONH or NHCO,
X is =NH—, O or —CH$_2$—,
Y is NH or O,
$R^6$ is a mono- or binuclear heterocycle which has 1-4 N, O and/or S atoms and which can be unsubstituted or mono-, di- or trisubstituted by Hal, A, —CO—A, OH, CN, COOH, COOA, CONH$_2$, NO$_2$, =NH or =O,
$R^{10}$ is H, alkyl with 1-6 C atoms, camphor-10-yl or benzyl,
$R^{11}$ is H,
A is unsubstituted alkyl with 1-6 C atoms and
m, n are each independently of one another 0, 1 or 2;
in IIe)
$R^1$ is H or alkyl with 1-6 C atoms,
$R^2$ is R$^{10}$, CO—R$^{10}$, COOR$^{10}$ or SO$_2$R$^{10}$,
$R^3$ is H,
$R^4$ is H or =O,
$R^5$ is R$^6$,
W, Z are each independently of one another absent, C(=O), NH, CONH or NHCO,
X is —NH—, O or —CH$_2$—,
Y is NH or O,
$R^6$ is 1H-imidazol-2-yl, thiazol-2-yl, 1H-benzimidazol-2-yl, 2H-pyrazol-2-yl, 1H-tetrazol-5-yl, 2-imino-imidazolidin-4-on-5-yl, 1-A-1,5-dihydro-imidazol-4-on-2-yl, pyrimidin-2-yl or 1,4,5,6-tetrahydro-pyrimidin-2-yl,
$R^{10}$ is H, alkyl with 1-6 C atoms, camphor-10-yl or benzyl,
$R^{11}$ is H,
A is unsubstituted alkyl with 1-6 C atoms and
m, n are each independently of one another 0, 1 or 2;
in IIf)
$R^1$ is H or alkyl with 1-6 C atoms,
$R^2$ is $R^{10}$, CO—$R^{10}$, COO$R^{10}$ or SO$_2$$R^{10}$,
$R^3$ is H,
$R^4$ is H or =O,
$R^5$ is H$_2$N—C(=NH) or H$_2$N—C(=NH)—NH,
W, Z are each independently of one another absent, C(=O), NH, CONH or NHCO,
X is —NH—, O or —CH$_2$—,
Y is NH or O,
$R^{10}$ is Ar,
$R^{11}$ is H,
A is unsubstituted alkyl or cycloalkyl with 1-15 C atoms and
m, n are each independently of one another 0, 1 or 2;
in IIg)
$R^1$ is H or alkyl with 1-6 C atoms,
$R^2$ is $R^{10}$, CO—$R^{10}$, COO$R^{10}$ or SO$_2$$R^{10}$,
$R^3$ is H,
$R^4$ is H or =O,
$R^5$ is $R^6$,
W, Z are each independently of one another absent, C(=O), NH, CONH or NHCO,
X is —NH—, O or —CH$_2$—,
Y is NH or O,
$R^6$ is a mono- or binuclear heterocycle which has 1-4 N, O and/or S atoms and which can be unsubstituted or mono-, di- or trisubstftuted by Hal, A, —CO—A, OH, CN, COOH, COOA, CONH$_2$, NO$_2$, =NH or =O,
$R^{10}$ is Ar,
$R^{11}$ is H,
A is unsubstituted alkyl or cycloalkyl with 1-15 C. atoms and
m, n are each independently of one another 0, 1 or 2.
in IIh)
$R^1$ is H or alkyl with 1-6 C atoms,
$R^2$ is CO—$R^{10}$, COO$R^{10}$ or SO$_2$$R^{10}$,
$R^3$ is H,
$R^4$ is H or =O,
$R^5$ is H$_2$N—C(=NH), H$_2$N—C(=NH)—NH, a mono- or binuclear heterocycle which has 1-4 N, O and/or S atoms and which can be unsubstituted or mono-, di- or trisubstituted by Hal, A, —CO—A, OH, CN, COOH, COOA, CONH$_2$, NO$_2$, =NH or =O, W, Z are each independently of one another absent, C(=O), NH, CONH or NHCO,
X is —CH$_2$—,
Y is NH or O,
$R^7$, $R^8$ is H
$R^{10}$ is A, Ar, aralkyl or Het,
$R^{11}$ is H,
A is unsubstituted alkyl or cycloalkyl with 1-15 C atoms and
m, n are each independently of one another 0, 1 or 2;

The compounds of formula II and subformulae IIa to IIg have been disclosed in DE 197 05 450 A1, the whole disclosure of which is hereby incorporated to the present application by reference. Accordingly, the substituents of formula II resp. subformulae IIa to IIg have the same meaning as defined for the substituents of formula I resp. subformulae Ia to Ig as disclosed on page 2, lines 3 to 43 resp. page 5, line 58 to page 7, line 30 of DE 197 05 450 A1. The definitions for the substituents are given on page 4, line 35 to page 5, line 56 of DE 197 05 450 A1.

More particularly preferred one of the following $\alpha_v\beta_3$ and/or $\alpha_v\beta_5$ inhibitors is used in the method of the present invention:

(2S)-2-[(R)-camphor-10-sulfonamido]-3-{3,4-dihydro-2-(3-guanidino-propyl)-( )-2H-1,4-benzoxazin-3-on-6-yl}propionic acid;

(2S)-2-benzyloxycarboxamido-3-(2-guanidinomethyl-1,4benzodioxan-6-yl)propionic acid;

(2S)-2-tert-butyloxycarboxamido-3-[3,4-dihydro-2-(2-guanidino-2-oxoethyl)-2H-1,4-benzoxazin-3-on-6-yl]propionic acid;

(2S)-2-benzyloxycarboxamido-3-2-guanidinoacet-amidomethyl-1,4-benzodioxan-6-yl)propionic acid;

(2S)-2-tert-butyloxycarboxamido-3-{3,4-dihydro-2-[N-(2-imidazolyl)-carbamoylmethyl]-2H-1,4-benzoxazin-3-on-6-yl)propionic acid;

(2S)-2-tert-butyloxycarboxamido-3-{3,4-dihydro-2-[N-(2-benzimidazolyl)-carbamoylmethy]-2H-1,4-benzoxazin-3-on-6-yl)propionic acid;

(2S)-2-tert-butyloxycarboxamido-3-{3,4-dihydro-2-[2-(2-imino-4-oxoimidazolidin-5-yl)ethyl]-2H-1,4-benzoxazin-3-on-6-yl}propionic acid;

(2S)-2-(2,2-dimethylpropyloxycarboxamido)-3-{3,4-dihydro-2-[N-(2-imidazolyl)carbamoylethyl]-(2S)-2H-1,4-benzoxazin-3-on-6-yl}propionic acid;

(2S)-2-[(R)-camphorsulfonamido]-3-{3,4-dihydro-2-[N-(2-benzimidazolyl)carbamoylmethyl]-2H-1,4-benzoxazin-3-on-6-yl)propionic acid (2S)-3-{2-[3-(1H-imidazol-2-ylamino)propyl]-chroman-6-yl}-2-(2,2-dimethylpropoxycarboxamido)propionic acid;

(2S)-3-{2-[3-(1H-imidazol-2-ylamino)propyl]-chroman-6-yl}-2-(butylsulfonamido)-propionic acid;

(2S)-3-{2-[3-(1H-imidazol-2-ylamino)propyl]-chroman-6-yl}-2-(4-fluorphenylsulfonamid)-propionic acid;

(2S)-3-{2-[3-(pyridin-2-ylamino)propyl]-chroman-6-yl}-2-(2,4,6-trimetylphenylsulfonamido)propionic acid;

(2S)-3-{2-[3-(pyridin-2-ylamino)propyl]-chroman-6-yl}-2-(2,2-dimethylpropoxycarboxamido)propionic acid;

(2S)-3-{2-[3-(1H-imidazol-2-ylamino)propyl]-chroman-6-yl}-2-(tert.butyloxycarboxamido)-propionic acid;

(2S)-3-{2-[3-(1H-imidazol-2-ylamino)propyl]-chroman-6-yl}-2-(diphenylmethylsulfonamido)-propionic acid;

and their physiologically acceptable salts.

Most preferred are (2S-2-(2,2-dimethylpropyloxycarboxamido)-3-{3,4-dihydro-2-[N-(2-imidazolyl)carbamoyl-ethyl]-(2S)-2H-1,4-benzoxazin-3-on-6-yl}propionic acid (2S)-2-(2,2-dimethylpropyloxycarboxamido)-3-{3,4-dihydro-2-[N-(2-imidazolyl)carbamoyl-ethyl]-(2R-2H-1,4-benzoxazin-3-on-6-yl}propionic acid (2S)-3-{2-[3-(1H-imidazol-2-ylamino)propyl]-chroman-6-yl}-2-(2,2-dimethylpropoxycarboxamido)propionic acid;

(2S)-3-{2-[3-(1H-imidazol-2-ylamino)propyl]-chroman-6-yl}-2-(butylsulfonamido)-propionic acid; and (2S)-2-[(R)-camphorsulfonamido]-3-{3,4-dihydro-2-[N-(2-benzimidazolyl)-carbamoylmethyl]-2H-1,4-benzoxazin-3-on-6-yl)propionic acid:

In one further preferred embodiment of the method of invention the $\alpha_v\beta_3$ and/or $\alpha_v\beta_5$ inhibitors to be used in the method for prophylaxis or treatment of eye diseases are compounds of formula III

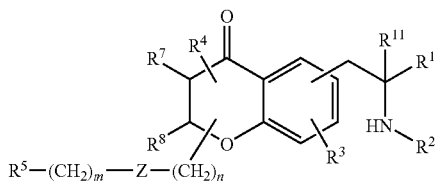

in which
$R^1$ is $CH_2OR^{10}$, $COOR^{10}$, $CONHR^{10}$ or $CON(R^{12})_2$,
$R^2$ is $R^{10}$, CO—$R^{10}$, CO—$R^6$, $COOR^6$, $COOR^{10}$, $SO_2R^6$, $SO_2R^{10}$, $CONHR^6$, $CON(R^6)_2$, $CONHR^{10}$ or $CON(R^{12})_2$,
$R^3$ is H, Hal, $NHR^{10}$, $N(R^{12})_2$, NH-acyl, —O-acyl, CN, $NO_2$, $OR^{10}$, $SR^{10}$, $SO_2R^{10}$, $SO_3R^{10}$, $COOR^{10}$, $CONHR^6$, $CON(R^6)_2$, $CONHR^{10}$ or $CON(R^{12})_2$,
$R^4$ is H, A, Ar or aralkylene having 7-14 C atoms,
$R^5$ is $NH_2$, $H_2N$—C(=NH) or $H_2N$—(C=NH)—NH, where the primary amino groups can also be provided with conventional amino protective groups, or can be mono-di- or trisubstituted by $R^{10}$, CO—$R^{10}$, $COOR^{10}$ or $SO_2R^{10}$, or $R^6$—NH—,
$R^6$ is a mono- or binuclear heterocycle having 1 to 4 N, O and/or S atoms, which can be unsubstituted or mono-, di- or trisubstituted by Hal, A, —CO—A, OH, CN, COOH, COOA, $CONH_2$, $NO_2$, =NH or =O,
$R^7$, $R^8$ in each case independently of one another is absent or is H,
$R^7$ and $R^8$ together are also a bond,
Z is absent, O, S, NH, $NR^1$, C(=O), CONH, NHCO, C(=S)NH, NHC(=S), C(=S), $SO_2NH$, $NHSO_2$ or CA=CA',
$R^9$ is H, Hal, $OR^{11}$, $NH_2$, $NHR^{12}$, $N(R^{12})_2$, NHAcyl, OAcyl, CN, $NO_2$, $SR^{11}$, $SOR^{12}$, $SO_2R^{12}$ or $SO_3H$,
$R^{10}$ is H, A, Ar or aralkylene having 7-14 C atoms,
$R^{11}$ is H or alkyl with 1-6 C atoms,
$R^{12}$ is alkyl having 1-6 C atoms,
A is H or alkyl having 1-15 C atoms or cycloalkyl having 3-15 C atoms, which is unsubstituted or is mono-, di- or trisubstituted by $R^9$ and in which one, two or three methylene groups can also be replaced by N, O and/or S,
Ar is a mono- or binuclear aromatic ring system having 0, 1, 2, 3 or 4 N, O and/or S atoms, which is unsubstituted or mono-, di- or trisubstituted by A and/or $R^9$,
Hal is F, Cl, Br or I,
m, n in each case independently of one another are 0, 1, 2, 3 or 4, and their physiologically acceptable salts and solvates.

In this embodiment of the method of the present invention particularly preferred $\alpha_v\beta_3$ and/or $\alpha_v\beta_5$ inhibitors are used that can be expressed by the subformulae IIIa to IIIn, which otherwise correspond to formula III but in which
in IIIa)
$R^3$ is H;
in IIIb)
$R^3$ is H and
$R^2$ is $COOR^{10}$ or $SO_2R^{10}$;
in IIIc)
$R^3$ is H,
$R^2$ is $COOR^{10}$ or $SO_2R^{10}$ and
$R^{10}$ is H, A, Ar or aralkylene having 7-14 C atoms;

in IIId)
m is 0;
in IIIe)
m is 0 and
$R^3$ is H;
in IIIf)
$R^3$ is H,
$R^2$ is $COOR^{10}$ or $SO_2R^{10}$ and
m is 0;
in IIIg)
$R^3$ is H,
$R^2$ is $COOR^{10}$ or $SO_2R^{10}$ and
$R^{10}$ is H, A, Ar or aralkylene with 7-14 C atoms and
m is 0;
in IIIh)
$R^3$ is H,
$R^2$ is $COOR^{10}$ or $SO_2R^{10}$ and
$R^{10}$ is H, A, Ar or aralkylene having 7-14 C atoms and
A is H or unsubstituted alkyl having 1-15 C atoms or cycloalkyl having 3-15 C atoms;
Ar is phenyl or naphthyl and
m is 0;
in IIIi)
$R^6$ is a mono- or binuclear heterocycle having 1 to 4 N atoms, which can be unsubstituted or mono-, di- or trisubstituted by Hal, A, —CO—A, OH, CN, COOH, COOA, $CONH_2$, $NO_2$, =NH or =O,
in IIIj)
$R^3$ is H,
$R^2$ is $COOR^{10}$ or $SO_2R^{10}$ and
$R^{10}$ is H, A, Ar or aralkylene having 7-14 C atoms and
m is 0;
$R^6$ is a mono- or binuclear heterocycle having 1 to 4 N atoms, which can be unsubstituted or mono-, di- or trisubstituted by Hal, A, —CO—A, OH, CN, COOH, COOA, $CONH_2$, $NO_2$, =NH or =O;
in IIIk)
Z is absent;
in IIIl)
Z is absent and
$R^3$ is H;
in IIIm)
Z is absent,
$R^3$ is H and
$R^2$ is $COOR^{10}$ or $SO_2R^{10}$;
in IIIn)
Z is absent,
$R^3$ is H,
$R^4$ is H,
$R^2$ is $COOR^{10}$ or $SO_2R^{10}$;
$R^{10}$ is H, A, Ar or aralkylene having 7-14 C atoms,
$R^6$ is a mono- or binuclear heterocycle having 1 to 4 N atoms, which can be unsubstituted or mono-, or risubstituted by Hal, A, —CO—A, OH, CN, COOH, COOA, $CONH_2$, $NO_2$, =NH or =O,
A is H or unsubstituted alkyl having 1-6 C atoms,
Ar is phenyl or naphthyl and
m is 0.

The compounds of formula III and subformulae IIIa to IIIn have been disclosed in WO 00/26212 A1, the whole disclosure of which is incorporated to the present application by reference. Accordingly, the substituents of formula III resp. subformulae IIIa to IIIn have the same meaning as defined for the substituents of forrmula I resp. subformulae Ia to In as disclosed on page 1, line 5 to page 2, line 31 resp. page 13, line 20 to page 15, line 6 of WO 00/26212 A1. The definitions for the substituents are given on page 8, line 18 to page 13, line 10 of WO 00/26212 A1.

More particularly preferred one of the following $\alpha_v\beta_3$ and/or $\alpha_v\beta_5$ inhibitors is used in this embodiment of the method of the present invention:

(2S)-3-[2-(3-aminopropyl)-4-oxo-4H-chromen-6-yl]-2-(2,2-dimethylpropoxycarboxamido)propionic acid;

(2S)-3-[2-(3-guanidinopropyl)-4-oxo-4H-chromen-6-yl]-2-(2,2-dimethylpropoxycarboxamido)-propionic acid;

(2S)-3-{2-[3-(1H-imidazol-2-ylamino)propyl]-4-oxo-4H-chromen-6-yl}-2-(2,2-dimethylpropoxycarboxamido)propionic acid;

(2S)-3-{2-[3-(1H-imidazol-2-ylamino)propyl]-4-oxo-chroman-6-yl}-2-(2,2-dimethylpropoxycarboxamido) propionic acid;

(2S)-3-{2-[3-(pyridin-2-ylamino)propyl]-4-oxo-4H-chromen-6-yl}-2-(2,2-dimethylpropoxycarboxamido) propionic acid;

(2S)-3{2-[3-(1H-benzimidazol-2-ylamino)propyl]-4-oxo-4H-chromen-6-yl}-2-(2,2-dimethylpropoxycarboxamido)propionic acid;

(2S)-3-{2-[3-(1H-imidazol-2-ylamino)propyl]-4-oxo-4H-chromen-6-yl}-2-butylsulfonamidopropionic acid;

(2S)-3{2-[3-(pyridin-2-ylamino)propyl]-4-oxo-4H-chromen-6-yl}-2-(2,4,6-trimethylphenyl)sulfonamidopropionic acid or their physiologically acceptable salts and solvates.

Most preferred are (2S)-3-{2-[3-(1H-imidazol-2-ylamino)propyl]-4-oxo-4H-chromen-6-yl}-2-butylsulfonamidopropionic acid (2S)-3{2-[3-(1H-imidazol-2-ylamino)propyl]-4-oxo-4H-chromen-6-yl}-2-(2,2-dimethylpropoxycarboxamido) propionic acid and (2S)-3-{2-[3-(pyridin-2-ylamino)propyl]-4-oxo-4H-chromen-6-yl}-2-(2,4,6-trimethylphenyl)sulfonamidopropionic acid.

In one further preferred embodiment of the method of invention the $\alpha_v\beta_3$ and/or $\alpha_v\beta_5$ inhibitors to be used in the method for prophylaxis or treatment of eye diseases are compounds of formula IV

IV

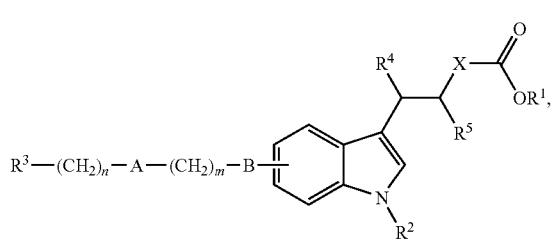

wherein

A and B are each independently of one another O, S, NH, $NR^7$, CO, CONH, NHCO or directly bond, X is alkylene having 1-2 C atoms, which is unsubstituted or monosubstituted by $R^4$ or $R^5$ or a direct bond, $R^1$ is H, Z or —$(CH_2)_o$—Ar, $R^2$ is H, $R^7$ or —C(O)Z, $R^3$ is $NHR^6$, —$NR^6$—C(=$NR^6$)—$NHR^6$, —C(=$NR^6$)—$NHR^6$, —$NR^6$—C(=$NR^9$)—$NHR^6$, —C(=$NR^9$)—$NHR^6$ or $Het^1$, $R^4$ or $R^5$ are each independently of one another H, oxo, $R^7$, —$(CH_2)_o$—Ar, —C(O)—$(CH_2)_o$—Ar, —C(O)—$(CH_2)_o$-$R^7$, —C(O)—$(CH_2)_o$-Het, Het, $NHR^6$, NHAr, NH-Het, $OR^7$, OAr, $OR^6$ or O-Het, $R^6$ is H, —C(O)$R^7$, —C(O)—Ar, $R^7$, $COOR^7$, COO—$(CH_2)_o$—Ar, $SO_2$—Ar, $SO_2R^7$ or $SO_2$-Het, $R^7$ is alkyl having 1 to 10 C atoms or cycloalkyl having 1 to 10 C atoms, $R^8$ is Hal, $NO_2$, CN, Z, —$(CH_2)_o$—Ar, $COOR^1$, $OR^1$, $CF_3$, $OCF_3$, $SO_2R^1$, $NHR^1$, $N(R^1)_2$, NH—C(O)$R^1$, $NHCOOR^1$ or C(O)$R^1$, $R^9$ is CN or $NO_2$, Z is alkyl having 1 to 6 C atoms, Ar is aryl, which is unsubstituted or substituted by $R^8$, Hal is F, Cl, Br or I, Het is saturated, partly of fully saturated mono- or bicyclic heterocyclic ring system having 5 to 10 atoms, which can contain 1 or 2 N atoms and/or 1 or 2 S or O atoms and wherein the heterocyclic ring system can be mono- or disubstituted by $R^8$, $Het^1$ is a mono or bicyclic aromatic heterocyclic ring system having 1 to 4 N atoms, which can be unsubstituted or mono- or disubstituted by Hal, $R^7$, $OR^7$, CN, NHZ or $NO_2$, n is 0, 1 or 2 m is 0, 1, 2, 3, 4, 5 or 6, o is 0, 1 or 2 as well as their physiologically acceptable salts and solvates.

In this embodiment of the method of invention particularly preferred $\alpha_v\beta_3$ and/or $\alpha_v\beta_5$ inhibitors are used that can be expressed by the subformulae IVa to IVi, which otherwise correspond to formula IV but in which in IVa X is a direct bond IVa

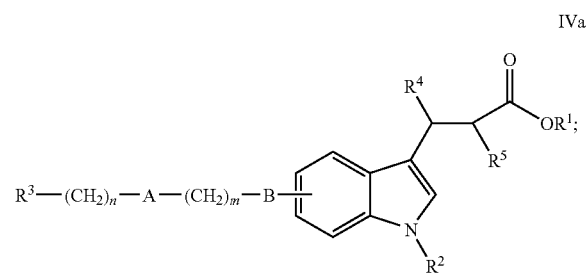

in IVb

X is a direct bond, $R^2$ is H, $R^5$ is H and $R^4$ is Ar

IVb

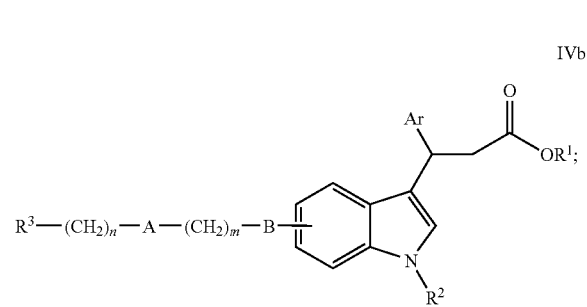

in IVc
  X is a direct bond,
  $R^5$ is H and
  $R^4$ is Ar or Het;
in IVd
  X is a direct bond,
  $R^5$ is H,
  B is O,
  A is NH,
  n is 0,
  m is 3 or 4,
  $R^3$ is Het and
  $R^4$ is Ar

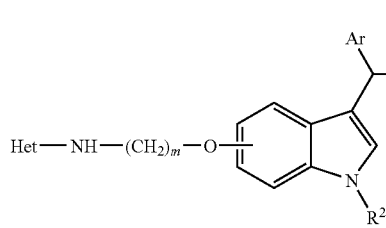

IVd in IVe
  X is a direct bond,
  $R^5$ is H,
  B is O,
  A is NH,
  n is 0,
  m is 3 or 4 and
  $R^3$ is Het

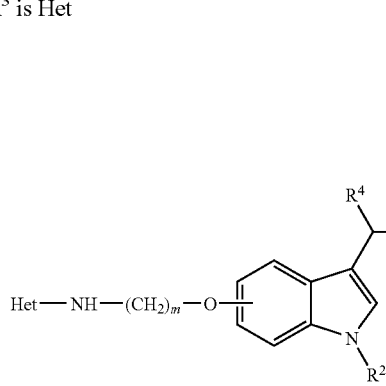

IVe in IVf
  X is methylene, which is unsubstituted or substituted by Ar,
  $R^2$ is H,
  $R^5$ is H oder Ar and
  $R^4$ is oxo

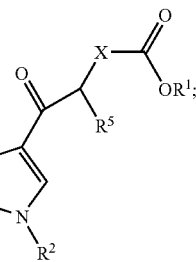

IVf in IVg
  X is methylene,

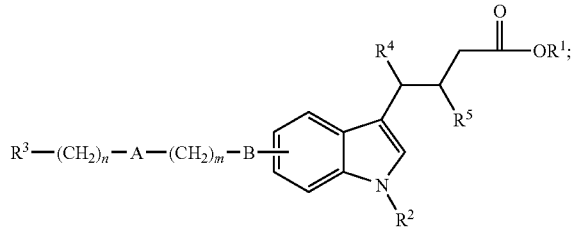

IVg in IVh
  X is methylene,
  $R^4$ is H or Ar,
  $R^5$ is H or Ar and
  $R^2$ is H;
in IVi
  X is methylene,
  $R^4$ is H or Ar,
  $R^5$ is H or Ar,
  B is O,
  A is NH,
  n is 0,
  m is 3 or 4
  $R^3$ is Het and
  $R^2$ is H

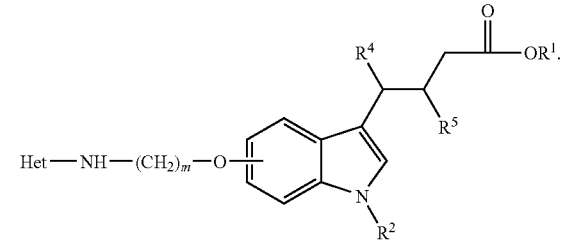

IVi

More particularly preferred the $\alpha_v\beta_3$ and/or $\alpha_v\beta_5$ inhibitor according to formula IV to be used in the method of the present invention is:

3-phenyl-3-{6-[3-(pyridine-2-ylamino)-propoxy]-1H-indole-3-yl}-propionic acid;

3-phenyl-3-{6-[4-(pyridine-2-ylamino)-butoxy]-1H-indole-3-yl}-propionic acid;

3-phenyl-3-{5-[4-(pyridine-2-ylamino)-butoxy]-1H-indole-3-yl}-propionic acid;

3-phenyl-3-{5-[3-(pyridine-2-ylamino)-propoxy]-1H-indole-3-yl}-propionic acid;

3-phenyl-3-[6-(pyridine-2-yl-amidocarboxymethoxy)-indole-3-yl]-propionic acid;

3-phenyl-3-[6-(benzimidazole-2-yl-amidocarboxymethoxy)-indole-3-yl]-propionic acid 3-phenyl-3-[6-(imidazole-2-yl-amidocarboxymethoxy)-indole-3-yl]-propionic acid or 3-Benzo[1,2,5]thiadiazol-5-yl-3-{6-[2-(6-methylamino-pyridin-2-yl)-ethoxy]-1H-indol-3-yl}-propionic acid as well as their physiologically acceptable salts and solvates.

Most preferred the $\alpha_v\beta_3$ and/or $\alpha_v\beta_5$ inhibitor according to formula IV to be used in the method of the present invention is 3-phenyl-3-{6-[3-(pyridine-2-ylamino)-propoxy]-1H-indole-3-yl}-propionic acid or 3-Benzo[1,2,5]thiadiazol-5-yl-3-{6-[2-(6-methylamino-pyridin-2-yl)-ethoxy]-1H-indol-3-yl}-propionic acid.

This compounds as well as the compounds of formula IV and subformulae IVa to IVi are disclosed in copending german patent application no. 100 06 139.7, the whole disclosure of which is hereby incorporated to the present application by reference. Accordingly, the substituents of formula IV and subformulae IVa to IVi have the same meaning as defined for the substituents of formula I resp. subformulae Ia to Ii as disclosed on page 1, line 3 to page 2, line 13 resp. page 17, line 4 to page 20, line 9 of german patent application no. 100 06 139.7. The definitions for the substituents are given on page 9, line 6 to page 16, line 28 of german patent application no. 100 06 139.7.

The particular suitability of the compounds as described hereinbefore for using in the method of treatment of eye diseases was experimentally confirmed for some representative compounds.

Inhibition of angiogenesis after intravitreal application of the compounds can be demonstrated by quantification of neovascularisation in the eye after stimulation of angiogenesis and subsequent intravitreal application of the $\alpha_v\beta_3$ and/or $\alpha_v\beta_5$ inhibitor. One model suitable for demonstrating the inhibiting effect of $\alpha_v\beta_3$ and/or $\alpha_v\beta_5$ inhibitor on angiogenesis is, for example, the rabbit corneal micropocket model described by Shaffer R. W. et al., in: Molecular, Cellular, and Clinical Aspects of Angiogenesis, Maragoudakis E. (ed.), Plenum Press, New York, 241ff. (1996). In this model angiogenesis is stimulated by implantation of Hydron pellets containing an angiogenesis stimulating cytokine like, for example, fibroblast growth factor (FGF) or vascular endothelial growth factor (VEGF) into the cornea. After implantation the active compound to be tested is administered by paralimbal intravitreal injection. Effect on neovascularisation is measured after predetermined time intervals by visual examination using a microscope, photographing and computer-assisted quantification of photographs.

As an alternative to application of cytokine induced angiogenesis, induction of angiogenesis can also be performed by laser photocoagulation, as, for example, described by Murata T. et al., IOVS, 41, 2309ff. (2000).

It is a further object of the invention to provide a composition suitable for the method for prophylaxis and treatment of diseases of the eye of a patient resulting from angiogenesis comprising injecting into the vitreous body of the eye of said patient a composition comprising a therapeutically effective amount of an $\alpha_v\beta_3$ and/or $\alpha_v\beta_5$ inhibitor sufficient to inhibit angiogenesis of the eye.

The formulation used for administration of the compound into the vitreous body of the eye can be any form suitable for application into the vitreous body by injection through a cannula with small diameter suitable for injection into the vitreous body. Examples for injectable application forms are solutions, suspensions or colloidal suspensions.

Compositions usable for injection into the vitreous body contain a physiologically tolerable carrier together with the relevant agent as described herein, dissolved or dispersed therein as an active ingredient. As used herein, the term "pharmaceutically acceptable" refers to compositions, carriers, diluents and reagents which represent materials that are capable of administration into the vitreous body of a mammal without the production of undesirable physiological effects. The preparation of a injectable pharmacological composition that contains active ingredients dissolved or dispersed therein is well understood in the art and need not be limited based on formulation. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, sorbitol, glycerol or the like and combinations thereof. In addition, if desired, the composition can contain minor amounts of auxiliary substances such as wetting or emulsifying agents, pH buffering agents, and the like which enhance the effectiveness of the active ingredient. The composition can also contain viscosity enhancing agents like hyaluronic acid. The therapeutic composition of the present invention can include pharmaceutically acceptable salts of the components therein. Pharmaceutically acceptable salts include the acid addition salts that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred is the HCl salt.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, sorbitol and other solutes.

Depending from the application form the active compound liberates in an immediate or a sustained release manner. A sustained release formulation is preferred because the injection frequency can be reduced.

One possibility to achieve sustained release kinetics is embedding or encapsulating the active compound into nanoparticles. Nanoparticles can be administrated as powder, as powder mixture with added excipients or as suspensions. Colloidal suspensions of nanoparticles are preferred because they can easily be administrated through a cannula with small diameter.

Nanoparticles are particles with a diameter from about 5 nm to up to about 1000 nm. The term "nanoparticles" as it is used hereinafter refers to particles formed by a polymeric matrix in which the active compound is dispersed, also known as "nanospheres", and also refers to nanoparticles which are composed of a core containing the active compound which is surrounded by a polymeric membrane, also known as "nanocapsules". For administration into the vitreous body of the eye nanoparticles are preferred having a diameter from about 50 nm to about 500 nm, in particular from about 100 nm to about 200 nm.

Nanoparticles can be prepared by in situ polymerization of dispersed monomers or by using preformed polymers. Since polymers prepared in situ are often not biodegradable and/or contain toxicological serious byproducts nanoparticles from preformed polymers are preferred. Nanoparticles from preformed polymers can be prepared by different techniques, i.e. by emulsion evaporation, solvent displacement, salting-out and by emulsification diffusion.

Emulsion evaporation is the classical technique for preparation of nanoparticles from preformed polymers. According to this technique, the polymer and the active compounds are dissolved in a water-immiscible organic solvent, which is emulsified in an aqueous solution. The crude emulsion is then exposed to a high-energy source such as ultrasonic devices or passed through high pressure homogenizers or microfluidizers to reduce the particle size. Subsequently the organic solvent is removed by heat and/or vacuum resulting in formation of the nanoparticles with a diameter of about 100 nm to about 300 nm. Usually, methylene chloride and chloroform are used as organic solvent because of their water insolubility, good solubilizing properties, easy emulsification and high volatility. These solvents are, however, critical in view of their physiological tolerability. Moreover, the high shear force needed for particle size reduction can lead to damage of polymer and/or the active compound.

The solvent displacement process was firstly described in EP 0 274 961 A1. In this process the active compound and the polymer are dissolved in an organic solvent which is miscible with water in all proportions. This solution is introduced in an aqueous solution containing a stabilizer under gentle agitation resulting in spontaneous formation of nanoparticles. Examples for suitable organic solvents and stabilizer are acetone or ethanol resp. polyvinyl alcohol. Advantageously chlorinated solvents and shear stress can be avoided. The mechanism of formation of nanoparticles has been explained by interfacial turbulence generated during solvent displacement (Fessi H. et al., Int. J. Pharm. 55 (1989) R1-R4). Recently, a solvent displacement technique was disclosed by WO 97/03657 A1, in which the organic solvent containing the active compound and the polymer is introduced into the aqueous solution without agitation.

The salting-out technique was firstly described in WO 88/08011 A1. In this technique a solution of a water-insoluble polymer and an active compound in a water-soluble organic solvent, especially acetone, is mied with a concentrated aqueous viscous solution or gel containing a colloidal stabilizer and a salting-out agent. To the resulting oil-in-water emulsion water is added in a quantity sufficient to diffuse into the aqueous phase and to induce rapid diffusion of the organic solvent into the aqueous phase leading to interfaciale turbulence and formation of nanoparticles. The organic solvent and the salting-out agent remaining in the suspension of nanoparticles are subsequently eliminated by repeated washing with water. Alternatively, the solvent and salting-out agent can be eliminated by cross-flow filtration.

In emulsification-diffusion process the polymer is dissolved in a water-saturated partially water-soluble organic solvent. This solution is mixed with an aqueous solution containing a stabilizer resulting in an oil-in-water emulsion. To this emulsion water is added causing the solvent to diffuse into the aqueous external phase accompanied with formation of nanoparticles. During particle formation each emulsion droplet leads to several nanoparticle. As this phenomenon cannot be fully explained by convection effect caused by interfacial turbulence, it has been proposed that diffusion of organic solvent from the droplets of the crude emulsion carries molecules of active compound and polymer phase into the aqueous phase resulting in supersaturated local regions, from which the polymer aggregates in the form of nanoparticles (Quintanar-Guerrero D. et al. Colloid. Polym. Sci. 275 (1997) 640-647). Advantageously, pharmaceutically acceptable solvents like propylene carbonate or ethyl acetate can be used as organic solvents.

With the methods described above nanoparticles can be formed with various types of polymers. For use in the method of the present invention, which involves injection of the formulation into the vitreous body of the eye, nanoparticles made from biocompatible polymers are preferred. The term "biocompatible" refers to material which, after introducing in a biological environment, have no serious effects to the biological environment. From biocompatible polymers those polymers are especially preferred which are also biodegradable. The term "biodegradable" refers to material which, after introducing in a biological environment, is enzymatically or chemically degraded into smaller molecules which can be eliminated subsequently. Biodegradable polymers are well known by the person skilled in the art. Examples are polyesters from hydroxycarboxylic acids such as poly(lactic acid) (PLA), poly(glycolic acid) (PGA), polycaprolactone (PCL), copolymers of lactic acid and glycolic acid (PLGA), copolymers of lactic acid and caprolactone, polyepsilon caprolactone, polyhyroxy butyric acid and poly(ortho)esters, polyurethanes, polyanhydrides, polyacetals, polydihydropyrans, polycyanoacrylates, natural polymers such as alginate and other polysaccharides including dextran and cellulose, collagen and albumin.

Liposomes are a further drug delivery system which is easily injectable. Accordingly, in the method of invention the active compounds can also be administered into the vitreous body of the eye in the form of a liposome delivery system. Liposomes are well-known by a person skilled in the art. Liposomes can be formed from a variety of phospholipids, such as cholesterol, stearylamine of phosphatidylcholines. Liposomes being usable for the method of invention encompass all types of liposomes including, but not limited to, small unilamellar vesicles, large unilamellar vesicles and multilamellar vesicles.

EXAMPLE

The effect of intravitreal application of an $\alpha_v\beta_3$ and/or $\alpha_v\beta_5$ inhibitor was examined in rabbit corneal micropocket model as described by Shaffer R. W. (see above). As an example for an $\alpha_v\beta_3$ and/or $\alpha_v\beta_5$ inhibitor 2-(2,2-dimethylpropyloxycarboxamido)-3{3,4-dihydro-2-[N-(2-imidazoly)-carbamoyl-ethyl]-2H-1,4-benzoxazin-3-on-6-yl}propionic acid was used in the experiment. For induction of angiogenesis Hydron pellets containing basic fibroblast growth factor (bFGF) were used. Preparation of bFGF containing implants was performed by casting Hydron [poly(hydroxyethyl)methacrylate] in specially prepared Teflon pegs that have a 2.5 mm core drilled into their surfaces. Approximately 12 µl of casting material was placed into each peg and polymerized overnight in a sterile hood, then sterilized by ultraviolet irradiation.

The experiment consisted of 10 animals; in each eye of the animals one individual pellet was implanted into a surgically created "pocket" in the mid stroma of the rabbit cornea. The surgical procedure was done under sterile technique using a Moeller-Wedel Microflex operating microscope (Haag-Streit Company, Germany) equipped with a beamsplitter and camera for photographically recording individual corneas. A 69

Beaver blade was used to create a 3 mm by 5 mm "pocket" to a depth of half the corneal thickness. The stroma was dissected peripherally using an spatula and the pellet implanted with its peripheral margin 2 mm from limbus. Immediately after implantation of bFGF-containing Hydron pellets 5 of the 10 animals received in each eye 100 μl of a drug solution consisting of 2.0 mg/ml 2-(2,2-dimethylpropyloxycarboxamido)-3-{3,4-dihydro-2-[N-(2-imidazolyl)-carbamoylethyl]-2H-1,4-benzoxazin-3-on-6-yl}propionic acid solubilized in physiological saline by intravitreal injection. For comparison the same procedure was performed in the other 5 animals using saline only. Following implantation the eyes Were photographed and the area of neovascularisation measured after predetermined intervals. The results obtained 5 and 7 days post implantion are presented in tables 1 and 2. An overview of the results obtained 5, 7, 10, and 14 days post implantation are presented in table 1.

TABLE 1 single (day 0) intravitreal, 100 μL, 20 mg/mL drug = 2 mg/eye

| | days post implantation | | | | | | |
|---|---|---|---|---|---|---|---|
| | 5 | | 7 | | 10 | | 14 |
| | inhibition [%] | | | | | | |
| | 56.3 | | 13.4 | | 45.8 | | 40.0 |
| | p < 0.005 | | p < 0.233 | | p < 0.002 | | p < 0.005 |
| | Control | Drug | Control | Drug | Control | Drug | Control | Drug |
| mean area [mm²] | 3.91 | 1.71 | 5.37 | 4.65 | 9.41 | 5.10 | 16.56 | 9.94 |
| S.D. | 1.84 | 1.29 | 1.86 | 2.11 | 2.97 | 2.26 | 5.40 | 3.31 |
| CV % | 47.06 | 75.44 | 34.64 | 45.38 | 31.56 | 44.31 | 32.61 | 33.30 |
| n | 10 | 9 | 10 | 9 | 10 | 9 | 10 | 7 |

Table 1 Effect of a Single (Day 0) Intravitreal Injection of 2-(2,2-dimethylpropyloxycarboxamido)-3-{3,4-dihydro-2-[N-(2-imidazolyl)-carbamoylethyl]-2H-1,4-benzoxazin-3-on-6-yl}propionic acid on bFGF-Stimulated Corneal Angiogenesis, 5, 7, 10, 14 Days Post-Implantation The results obtained clearly demonstrate the advantagous effect of the present invention. Although only a single dosis of $\alpha_v\beta_3$ and/or $\alpha_v\beta_5$ inhibitor was given and drug formulation was only a solution, strong inhibition of neovascularization was performed over many days.

What claimed is:

1. A method for treatment of a disease of the eye of a patient resulting from angiogenesis and neovascularization in the eye comprising injecting into the vitreous body of the eye of said patient a composition comprising a therapeutically effective mount of an $\alpha_v\beta_3$ and/or $\alpha_v\beta_5$ inhibitor sufficient to inhibit angiogenesis and inhibit neovascularization in the treated eye, wherein the $\alpha_v\beta_3$ and/or $\alpha_v\beta_5$ inhibitor is a compound of formula II:

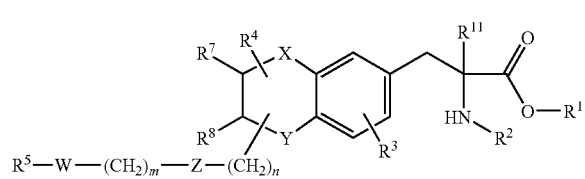

II wherein
R¹ is H, alkyl having 1-6 C atoms or benzyl,
R² is R¹⁰, CO—R¹⁰, COOR⁶, COOR¹⁰, SO₂R⁶ or SO₂R¹⁰,
R³ is H, Hal, OA, NHR¹⁰, N(R¹⁰)₂, —NH-acyl, —O-acyl, CN, NO₂, OR¹⁰, SR¹⁰, R² or CONHR¹⁰,
R⁴ is H, =O, =S, C₁-C₆-alkyl or acyl,
R⁵ is NH₂, H₂N—C(=NH) or H₂N—(C=NH)—NH, where the primary amino groups are optionally provided with conventional amino protective groups and optionally mono-, di- or tri-substituted by R¹⁰, CO—R¹⁰, COOR¹⁰ or SO₂R¹⁰, or R⁶,
R⁷, R⁸ are each independently of one another absent or H, or
R⁷ and R⁸ together are a bond,
X, Y are each independently of one another =N—, —N—, O, S, —CH₂— or =C—, with the proviso that at least one of X and Y is =N—, —N—, O or S,
W, Z are each independently of one another absent, O, S, NR¹, C(=O), CONH, NHCO, C(=S)NH, NHC(=S), C(=S), SO₂NH, NHSO₂ or CA=CA',
R⁶ is a mono- or binuclear heterocycle which has 1 to 4 N, O and/or S atoms and is unsubstituted or mono-, di- or tri-substituted by Hal, A, —CO—A, OH, CN, COOH, COOA, CONH₂, NO₂, =NH or =O,
R⁹ is H, Hal, OA, NHA, NAA', NHacyl, Oacyl, CN, NO₂, SA, SOA, SO₂A, SO₂Ar or SO₃H,
R¹⁰ is H, A, Ar or aralkyl having 7-14 C atoms,
R¹¹ is H or alkyl having 1-6 C atoms,
A, A' are each independently of one another H or unsubstituted or mono-, di- or tri-R⁹-substituted alkyl or cycloalkyl, each of which has 1-15 C atoms and in which one, two or three methylene groups can be replaced by N, O and/or S,
Ar is unsubstituted or mono-, di- or tri-A- and/or R⁹-substituted mono- or binuclear aromatic ring system having 0, 1, 2, 3 or 4 N, O and/or S atoms,
Hal is F, Cl, Br or I and
m, n are each independently of one another 0, 1, 2, 3 or 4; or a physiologically acceptable salt thereof.

2. A method of claim 1 wherein said therapeutically effective amount is from about 0.5 μg to 5 mg.

3. A method of claim 1 wherein said eye disease is diabetic retinopathy.

4. A method of claim 1 wherein said eye disease is macular degeneration.

5. A method of claim 1 wherein said eye disease is myopia.

6. A method of claim 1 wherein said eye disease is ocular histoplasmosis.

7. A method of claim 1 wherein the $\alpha_v\beta_3$ and/or $\alpha_v\beta_5$ inhibitor is selected from the group consisting of compounds of formula II wherein the variables are defined by IIa to IIg below:
in IIa)
R¹ is H or alkyl with 1-6 C atoms,
R² is R¹⁰, CO—R¹⁰, COOR¹⁰ or SO₂R¹⁰,
R³ is H,
R⁴ is H or =O,
R⁵ is H₂N—C(=NH) or H₂N—C(=NH)—NH,
W, Z are each independently of one another absent, C(=O), NH, CONH or NHCO,
X is —NH—, O or —CH₂—,
Y is NH or O,
R¹⁰ is H, A or benzyl,
R¹¹ is H,
A is unsubstituted alkyl or cycloalkyl with 1-15 C atoms and
m, n are each independently of one another 0, 1 or 2;

in IIb)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is $R^6$,
- W, Z are each independently of one another absent, C(=O), NH, CONH or NHCO,
- X is —NH—, O or —CH$_2$—,
- Y is NH or O,
- $R^6$ is a mono- or binuclear heterocycle which has 1-4 N, O and/or S atoms and which can be unsubstituted or mono-, di- or trisubstituted by Hal, A, —CO—A, OH, CN, COOH, COOA, CONH$_2$, NO$_2$, =NH or =O,
- $R^{10}$ is H, A or benzyl,
- $R^{11}$ is H,
- A is unsubstituted alkyl or cycloalkyl with 1-15 C atoms and
- m, n are each independently of one another 0, 1 or 2;

in IIc)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is H$_2$N—C(=NH) or H$_2$N—C(=NH)—NH,
- W, Z are each independently of one another absent, C(=O), NH, CONH or NHCO,
- X is —NH—, O or —CH$_2$—,
- Y is NH or O,
- A is alkyl with 1-6 C atoms,
- $R^{10}$ is H, alkyl with 1-6 C atoms, camphor-10-yl or benzyl,
- $R^{11}$ is H,
- m, n are each independently of one another 0, 1 or 2;

in IId)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is $R^6$,
- W, Z are each independently of one another absent, C(=O), NH, CONH or NHCO,
- X is =NH—, O or —CH$_2$—,
- Y is NH or O,
- $R^6$ is a mono- or binuclear heterocycle which has 1-4 N, O and/or S atoms and which is unsubstituted or mono-, di- or trisubstituted by Hal, A, —CO—A, OH, CN, COOH, COOA, CONH$_2$, NO$_2$, =NH or =O,
- $R^{10}$ is H, alkyl with 1-6 C atoms, camphor-10-yl or benzyl,
- $R^{11}$ is H,
- A is unsubstituted alkyl with 1-6 C atoms and
- m, n are each independently of one another 0, 1 or 2;

in IIe)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is $R^6$,
- W, Z are each independently of one another absent, C(=O), NH, CONH or NHCO,
- X is —NH—, O or —CH$_2$—,
- Y is NH or O,
- $R^6$ is 1H-imidazol-2-yl, thiazol-2-yl, 1H-benzimidazol-2-yl, 2H-pyrazol-2-yl, 1H-tetrazol-5-yl, 2-imino-imidazolidin-4-on-5-yl, 1-A-1,5-dihydro-imidazol-4-on-2-yl, pyrimidin-2-yl or 1,4,5,6-tetrahydro-pyrimidin-2-yl,
- $R^{10}$ is H, alkyl with 1-6 C atoms, camphor-10-yl or benzyl,
- $R^{11}$ is H,
- A is unsubstituted alkyl with 1-6 C atoms and
- m, n are each independently of one another 0, 1 or 2;

in IIf)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is H$_2$N—C(=NH) or H$_2$N—C(=NH)—NH,
- W, Z are each independently of one another absent, C(=O), NH, CONH or NHCO,
- X is —NH—, O or —CH$_2$—,
- Y is NH or O,
- $R^{10}$ is Ar,
- $R^{11}$ is H,
- A is unsubstituted alkyl or cycloalkyl with 1-15 C atoms and
- m, n are each independently of one another 0, 1 or 2;

in IIg)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is $R^6$,
- W, Z are each independently of one another absent, C(=O), NH, CONH or NHCO,
- X is —NH—, O or —CH$_2$—,
- Y is NH or O,
- $R^6$ is a mono- or binuclear heterocycle which has 1-4 N, O and/or S atoms and which is unsubstituted or mono-, di- or trisubstituted by Hal, A, —CO—A, OH, CN, COOH, COOA, CONH$_2$, NO$_2$, =NH or =O,
- $R^{10}$ is Ar,
- $R^{11}$ is H,
- A is unsubstituted alkyl or cycloalkyl with 1-15 C. atoms and
- m, n are each independently of one another 0, 1 or 2 in IIh)
- $R^1$ is H or alkyl with 1-6 C atoms,
- $R^2$ is $R^{10}$, CO—$R^{10}$, COO$R^{10}$ or SO$_2R^{10}$,
- $R^3$ is H,
- $R^4$ is H or =O,
- $R^5$ is H$_2$N—C(=NH), H$_2$N—C(=NH)—NH, a mono- or binuclear heterocycle which has 1-4 N, O and/or S atoms and which is unsubstituted or mono-, di- or trisubstituted by Hal, A, —CO—A, OH, CN, COOH, COOA, CONH$_2$, NO$_2$, =NH or =O,
- W, Z are each independently of one another absent, C(=O), NH, CONH or NHCO,
- X is —CH$_2$—,
- Y is NH or O,
- $R^7$, $R^8$ is H
- $R^{10}$ is A, Ar, aralkyl or Het,
- $R^{11}$ is H,
- A is unsubstituted alkyl or cycloalkyl with 1-15 C atoms and
- m, n are each independently of one another 0, 1 or 2.

8. A method according to claim 1 wherein the $\alpha_v\beta_3$ and/or $\alpha_v\beta_5$ inhibitor is a compound selected from the group consisting of:

(2S)-2-[(R)-camphor-10-sulfonamido]-3-{3,4-dihydro-2-(3-guanidino-propyl)-(2H-1,4-benzoxazin-3-on-6-yl}propionic acid;
(2S)-2-benzyloxycarboxamido-3-(2-guanidinomethyl-1,4-benzodioxan-6-yl)propionic acid;
(2S)-2-tert-butyloxycarboxamido-3-[3,4-dihydro-2-(2-guanidino-2-oxoethyl)-2H-1,4-benzoxazin-3-on-6-yl]propionic acid;
(2S)-2-benzyloxycarboxamido-3-(2-guanidinoacet-amidomethyl-1,4-benzo-dioxan-6-yl)propionic acid;
(2S)-2-tert-butyloxycarboxamido-3-{3,4-dihydro-2-[N-(2-imidazolyl)-carbamoylmethyl]-2H-1,4-benzoxazin-3-on-6-yl)propionic acid;
(2S)-2-tert-butyloxycarboxamido-3-{3,4-dihydro-2-[N-(2-benzimidazolyl)-carbamoylmethyl]-2H-1,4-benzoxazin-3-on-6-yl)propionic acid;
(2S)-2-tert-butyloxycarboxamido-3-{3,4-dihydro-2-[2-(2-imino-4-oxoimidazolidin-5-yl)ethyl]-2H-1,4-benzoxazin-3-on-6-yl}propionic acid;
(2S)-2-(2,2-dimethylpropyloxycarboxamido)-3-{3,4-dihydro-2-[N-(2-imidazolyl)carbamoylethyl]-(2S)-2H-1,4-benzoxazin-3-on-6-yl}propionic;
(2S)-2-[(R)-camphorsulfonamido]-3-{3,4-dihydro-2-[N-(2-benzimidazolyl)-carbamoylmethyl]-2H-1,4-benzoxazin-3-on-6-yl)propionic acid
(2S)-3-{2-[3-(1H-imidazol-2-ylamino)propyl]-chroman-6-yl}-2-(2,2-dimethylpropoxycarboxamido)propionic acid;
(2S)-3-{2-[3-(1H-imidazol-2-ylamino)propyl]-chroman-6-yl}-2-(butylsulfonamido)-propionic acid;
(2S)-3-{2-[3-(1H-imidazol-2-ylamino)propyl]-chroman-6-yl}-2-(4-fluorphenylsulfonamido)-propionic acid;
(2S)-3-{2-[3-(pyridin-2-ylamino)propyl]-chroman-6-yl}-2-(2,4,6-trimetylphenylsulfonamido)propionic acid;
(2S)-3-{2-[3-(pyridin-2-ylamino)propyl]-chroman-6-yl}-2-(2,2-dimethylpropoxycarboxamido)propionic acid;
(2S)-3-{2-[3-(1H-imidazol-2-ylamino)propyl]-chroman-6-yl}-2-(tert.butyloxycarboxamido)-propionic acid;
(2S)-3-{2-[3-(1H-imidazol-2-ylamino)propyl]-chroman-6-yl}-2-(diphenylmethylsulfonamido)-propionic acid;
and their physiologically acceptable salts.

9. A method according to claim 1 wherein the $\alpha_v\beta_3$ and/or $\alpha_v\beta_5$ inhibitor is:
(2S)-2-(2,2-dimethylpropyloxycarboxamido)-3-{3,4-dihydro-2-[N-(2-imidazolyl)-carbamoylethyl]-(2S)-2H-1,4-benzoxazin-3-on-6-yl}propionic acid
(2S)-3-{2-[3-(1H-imidazol-2-ylamino)propyl]-chroman-6-yl}-2-(2,2-dimethylpropoxycarboxamido)propionic acid;
(2S)-3-{2-[3-(1H-imidazol-2-ylamino)propyl]-chroman-6-yl}-2-(butylsulfonamido)-propionic acid; or
(2S)-2-[(R)-camphorsulfonamido]-3-{3,4-dihydro-2-[N-(2-benzimidazolyl)-carbamoylmethyl]-2H-1,4-benzoxazin-3-on-6-yl)propionic acid.

10. A method of claim 1 wherein the composition comprises nanoparticles containing the therapeutically effective amount of the $\alpha_v\beta_3$ and/or $\alpha_v\beta_5$ inhibitor sufficient to inhibit angiogenesis of the eye.

11. A method of claim 10 wherein the nanoparticles further contain a biocompatible polymer.

12. A method of claim 10 wherein the nanoparticles further contain a biodegradable polymer.

13. A method of claim 11 wherein the polymer is poly(lactic acid) (PLA), poly(glycolic acid) (PGA), polycaprolactone (PCL), a copolymer of lactic acid and glycolic acid (PLGA), a copolymer of lactic acid and caprolactone, poly-epsilon caprolactone, polyhyroxy butyric acid, a poly(ortho) ester, a polyurethane, a polyanhydride, a polyacetal, a polydihydropyran or a polycyanoacrylate.

14. A method of claim 10 wherein the composition comprises a liquid medium wherein the nanoparticles are being dispersed thereby forming a colloidal suspension.

15. A method of claim 10, wherein the nanoparticles have a diameter from about 10 nm to about 500 nm.

16. A method of claim 10, wherein the nanoparticles have a diameter from about 100 nm to about 200 nm.

17. A method of claim 10, wherein the nanoparticles are prepared by solvent displacement.

18. A method of claim 10, wherein the eye disease treated is diabetic retinopathy.

19. A method of claim 10, wherein the eye disease treated is macular degeneration.

20. A method of claim 10, wherein the eye disease treated is myopia.

21. A method of claim 10, wherein the eye disease treated is ocular histoplasmosis.

22. A method of claim 1 wherein said eye disease is exudative macular degeneration.

23. A method of claim 10 wherein said eye disease is exudative macular degeneration.

* * * * *

UNITED STATES PATENT AND TRADEMARK OFFICE
CERTIFICATE OF CORRECTION

PATENT NO. : 7,645,736 B2 Page 1 of 1
APPLICATION NO. : 11/510596
DATED : January 12, 2010
INVENTOR(S) : Bender et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 481 days.

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,645,736 B2
APPLICATION NO.   : 11/510596
DATED             : January 12, 2010
INVENTOR(S)       : Bender et al.

Page 1 of 1

It is certified that error appears in the above-identified patent and that said Letters Patent is hereby corrected as shown below:

Column 19, line 52 reads "mount of an $\alpha_v\beta_3$ and/or $\alpha_v\beta_5$ inhibitor sufficient to inhibit" should read -- amount of an $\alpha_v\beta_3$ and/or $\alpha_v\beta_5$ inhibitor sufficient to inhibit --

Signed and Sealed this
Fifteenth Day of February, 2011

David J. Kappos
*Director of the United States Patent and Trademark Office*